US006852977B2

(12) United States Patent
Hisazumi et al.

(10) Patent No.: US 6,852,977 B2
(45) Date of Patent: Feb. 8, 2005

(54) METHOD AND APPARATUS FOR IDENTIFYING PLASTIC

(75) Inventors: Takao Hisazumi, Ibaraki (JP); Teruo Gotoh, Takatsuki (JP); Shouichi Irie, Toyonaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 170 days.

(21) Appl. No.: 10/296,140

(22) PCT Filed: Mar. 26, 2002

(86) PCT No.: PCT/JP02/02879

§ 371 (c)(1),
(2), (4) Date: Nov. 20, 2002

(87) PCT Pub. No.: WO02/077618

PCT Pub. Date: Oct. 3, 2002

(65) Prior Publication Data

US 2003/0155511 A1 Aug. 21, 2003

(30) Foreign Application Priority Data

Mar. 27, 2001 (JP) ........................................ 2001-089477

(51) Int. Cl.⁷ .............................................. G01N 21/35
(52) U.S. Cl. ................................................. 250/339.12
(58) Field of Search ................................... 250/339.12

(56) References Cited

U.S. PATENT DOCUMENTS

| | | | |
|---|---|---|---|
| 5,172,182 A | 12/1992 | Sting et al. | |
| 5,216,244 A | 6/1993 | Esaki et al. | |
| 5,326,972 A | 7/1994 | Codella | |
| 5,381,228 A | * 1/1995 | Brace | 356/300 |
| 5,440,126 A | 8/1995 | Kemsley | |
| 5,965,889 A | 10/1999 | Brierley | |
| 6,025,417 A | * 2/2000 | Willett et al. | 524/17 |
| 6,141,100 A | * 10/2000 | Burka et al. | 356/451 |
| 6,563,119 B1 | * 5/2003 | Zoidis | 250/339.07 |
| 2003/0088028 A1 | * 5/2003 | Kambouris et al. | 525/242 |

FOREIGN PATENT DOCUMENTS

| | | |
|---|---|---|
| DE | 195 02 134 | 8/1996 |
| JP | 4-348257 | 12/1992 |
| JP | 5-322745 | 12/1993 |
| JP | 8-136449 | 5/1996 |
| JP | 10-500483 | 1/1998 |
| JP | 2000-046733 | 2/2000 |

OTHER PUBLICATIONS

Zachmann G.: "A Rapid and Dependable Identification System for Black Polymeric Materials", Journal of Molecular Structure, Mar. 15, 1995, vol. 348, pp. 453–456.

Broek, Van Den W.H.A.M. et al., "Application of a Spectroscopic Infrared Focal Plane Array Sensor for On–line Identification of Plastic Waste", Applied Spectroscopy, Jun. 1, 1997, US vol. 51, No. 6, pp. 856–865.

Anzano J.M., et al., "Laser–induced Plasma Spectroscopy for Plastic Identification", Polymer Engineering & Science, Nov. 2000, vol. 40, No. 11, pp. 2423–2429.

Murase J. et al., "Rapid Identification of Plastics by Pyrolysis Infrared Spectroscopy with a New Prolysis Probe", Applied Spectroscopy, Jun. 1999, US vol. 53, No. 6, pp. 745–747.

* cited by examiner

Primary Examiner—Constantine Hannaher
(74) Attorney, Agent, or Firm—Merchant & Gould P.C.

(57) ABSTRACT

A method for distinguishing a kind of plastic materials, by preparing a test piece of a plastic material; measuring an infrared spectrum of the test piece by attenuated total reflection spectroscopy; and comparing the obtained infrared spectrum with an infrared spectrum of a known plastic. The test piece has a section. The infrared spectrum of the test piece is measured by bringing the crystal for attenuated total reflection spectroscopy into contact with the section of the test piece.

26 Claims, 13 Drawing Sheets

METHOD AND APPARATUS FOR IDENTIFYING PLASTIC

TECHNICAL FIELD

The present invention relates to a method for distinguishing plastics for distinguishing a kind of plastic material easily, speedily and with high precision, and an apparatus therefore.

BACKGROUND ART

Recently, from the viewpoint of environmental protection and pollution control, there is a demand for reducing waste by promoting the use of recycled resources. In particular, since plastics are used for various applications of use, for example, household electrical appliances, automobiles, construction materials, etc., it is very important to promote the use of plastics as recycled resources.

In order to promote the recycling of plastics, firstly, it is necessary to distinguish the kind of waste plastics. Conventionally, as a method for distinguishing a kind of plastics, a near infrared spectroscopy and an infrared spectroscopy have been employed because of their abilities for highly precise analysis. An example of a general technique for such a spectroscopy includes a dispersed reflection method and a transmission method. However, with such techniques, if the plastic to be tested is black, all of near infrared rays and infrared rays are absorbed by plastics, so that necessary spectra cannot be obtained. Consequently, it was impossible to distinguish plastics.

As a method for distinguishing such plastics, the attenuated total reflection spectroscopy (hereinafter "ATR" will be referred to) is known. In this method, a sample having a low refractive index is brought into close contact with a crystal having a high refractive index; infrared rays are allowed to be incident in the interface between the crystal and the sample at an angle that is larger than the angle for causing a total reflection (critical angle); and the incident infrared rays are allowed to be reflected at the interface, and thereafter the reflected spectrum is measured.

By employing this ATR, every plastic material including a black-color sample can be distinguished with high precision. However, if the ATR is employed, in order to bring the sample into contact with the crystal, it was necessary to carry out sampling so that the sample has substantially the same area as the area of the surface of the crystal (for example, about 5 mm×about 20 mm) and the sample can be brought into contact with the entire crystal, and also necessary to shave the entire surface of the test piece so that an error in distinguishing is not caused by the influence of impurity or a surface treatment agent (for example, coating, plating, etc.) attached to the surface of the test piece. Thus, conventionally, in order to carry out the measurement by the ART, the test piece having a relatively large area was required. Furthermore, it was necessary to shave the entire surface of the test piece, and thus it took much time and efforts to prepare test pieces. In particular, for the purpose of recycling, continuous processing of a large amount of plastic materials is required, and thus the plastic materials are required to be distinguished simply and speedily. Therefore, the above-mentioned conventional method in which the preparation and pretreatment of test piece are required was not practical.

DISCLOSURE OF THE INVENTION

It is an object of the present invention to provide a method capable of preparing test pieces in a short time and easily and distinguishing plastic materials simply, speedily and with high precision, and an apparatus therefore.

In order to achieve the above-mentioned object, a first method for distinguishing plastics of the present invention includes preparing a test piece of a plastic material; measuring an infrared spectrum of the test piece by attenuated total reflection spectroscopy; and comparing the obtained infrared spectrum with an infrared spectrum of a known plastic, thereby distinguishing a kind of plastic materials, wherein the test piece has a section and the infrared spectrum of the test piece is measured by bringing a crystal for attenuated total reflection spectroscopy into contact with the section of the test piece.

With such a method, since a section of the test piece is a surface to be measured, the kind of plastic material can be distinguished with high precision without the influence of a surface treatment agent and impurity, etc. In addition, in this method, the test piece can be prepared easily by cutting and a particular pre-treatment for removing the surface treatment agent or impurity is not required. Therefore, the test piece can be prepared speedily and simply, and it is possible to distinguish plastic materials speedily and simply.

In the above-mentioned first method, it is preferable that the test piece is prepared by cutting the plastic material with a punching machine, a shearing machine, a band saw machine, or the like. With such a preferable example, it is possible to prepare test pieces speedily and simply.

In the above-mentioned first method, it is preferable that the infrared spectrum of the test piece is measured by bringing the crystal into contact with a part of the section corresponding to the inside portion of the plastic material and with a part of the section corresponding to the surface portion of the plastic material, the infrared spectrum obtained in the part corresponding to the inside portion of the plastic material is compared with the infrared spectrum of the known plastic, thereby distinguishing a kind of plastics constituting the test piece, and the infrared spectrum obtained in the part corresponding to the surface portion of the plastic material is compared with the infrared spectrum of the known plastic, surface treatment agent and impurity, thereby detecting the surface treatment agent and impurity attached to the test piece.

Note here that "a surface treatment agent" to be tested indicates a material attached to the surface of plastics for surface-treating plastic. Examples of the surface treatment agent include, for example, a coating material, a plating material, etc. Furthermore, an example of the impurity includes, for example, dust.

Furthermore, "detection of the surface treatment agent and impurity" includes detection of the presence or absence of the surface treatment agent and impurity as well as detection of the kind (component) and the amount of the surface treatment agent and impurity that are attached if any surface treatment agent and impurity are present.

Furthermore, "a part of the section corresponding to the surface portion of the plastic material" means the part corresponding to the surface layer of the plastic material before sampling. For example, a portion having a thickness of 0 to 0.3 mm from the surface is included in the surface layer of the plastic material. Furthermore, "a part of the section corresponding to the inside portion of the plastic material" means the part corresponding to the portion of the plastic excluding the above-mentioned surface layer.

With this preferable example, not only the kind of the plastic material but also the surface treatment agent and impurity attached to the surface can be detected. For example, when plastic materials are recycled, if the surface treatment agent and impurity attached to the plastic materials can be detected, it is possible to select the suitable method for removing the surface treatment agent and impurity based on the detection result, thus promoting recycling efficiency.

In the above-mentioned first method, it is preferable that the infrared spectrum of the test piece is measured by bringing the crystal into contact with the section of the test piece and with a part of the test piece other than the section, the infrared spectrum obtained in the section is compared with the infrared spectrum of the known plastic, thereby distinguishing a kind of plastics constituting the test piece, and the infrared spectrum obtained in the part other than the section is compared with the infrared spectrum of the known plastic, surface treatment agent and impurity, thereby detecting the surface treatment agent and impurity attached to the test piece.

Also with this preferable example, not only the kind of plastic material but also the surface treatment agent and impurity attached to the surface can be detected.

In order to achieve the above-mentioned object, a second method for distinguishing plastics of the present invention includes preparing a test piece of a plastic material, measuring an infrared spectrum of the test piece by attenuated total reflection spectroscopy, and comparing the obtained infrared spectrum with an infrared spectrum of a known plastic, thereby distinguishing a kind of plastic materials, wherein the infrared spectrum of the test piece is measured by applying pressure to the surface of the test piece, forming a concave portion on the surface of the test piece subjected to pressure and bringing the concave portion into contact with the crystal for attenuated total reflection spectroscopy.

In such a method, a concave portion is formed by presswork on the surface of the test piece and the infrared spectrum is measured on the inside surface of this concave portion. Therefore, even in the case where the surface treatment agent and impurity are attached to the plastic material, in the surface to be measured, the surface treatment agent and impurity are reduced or removed. Therefore, with reduced influence of the surface treatment agent and impurity, it is possible to distinguish a kind of plastic materials constituting the subject to be tested precisely. Furthermore, in this method, since the test piece can be prepared by cutting and presswork for a relatively short time and easily, it is possible to distinguish plastic materials speedily and simply.

Note here that "concave portion" includes not only a concave portion formed by plastic itself constituting a test piece, which has been deformed by pressure, but also a concave portion formed by partially reducing or removing the surface treatment agent or impurity.

In the second method, it is preferable that the infrared spectrum of the test piece is measured by bringing the crystal into contact with the concave portion of the test piece and with a part of the test piece in which the concave portion is not formed, the infrared spectrum obtained in the concave portion is compared with the infrared spectrum of the known plastic, thereby distinguishing the kind of plastic constituting the test piece; and the infrared spectrum obtained in the part in which the concave portion is not formed is compared with the infrared spectrum of the known plastic, surface treatment agent and impurity, thereby detecting the surface treatment agent and impurity attached to the test piece.

With this preferable example, not only the kind of plastic material but also the surface treatment agent and impurity attached to the surface can be detected.

In order to achieve the above-mentioned object, a third method for distinguishing plastics of the present invention includes preparing a test piece of a plastic material, measuring an infrared spectrum of the test piece by attenuated total reflection spectroscopy, and comparing the obtained infrared spectrum with an infrared spectrum of a known plastic, thereby distinguishing the kind of plastic material, wherein the infrared spectrum of the test piece is measured in a state in which a crystal for attenuated total reflection spectroscopy is brought into contact with the test piece, and a concave portion is formed in a part of the test piece being in contact with the crystal by the contact pressure between the test piece and the crystal.

With such a method, pressure is applied to a contact portion (that is, a surface to be measured) between the test piece and the crystal, so that a concave portion is formed. Therefore, even if the surface treatment agent and impurity are attached to the plastic material, in the surface to be measured, the surface treatment agent and impurity are reduced or removed. Therefore, with reduced influence of the treatment agent and impurity, it is possible to distinguish the kind of plastic material precisely. Furthermore, in this method, since the test piece can be prepared easily by cutting, it is possible to distinguish plastic materials speedily and simply.

In the third method, it is preferable that the infrared spectrum of the test piece is measured in a state in which the concave portion is formed in the part of the test piece being in contact with the crystal and in a state in which the concave portion is not formed in the part of the test piece being in contact with the crystal, the infrared spectrum obtained in a state in which the concave portion is formed is compared with the infrared spectrum of the known plastic, thereby distinguishing the kind of plastic constituting the test piece, and the infrared spectrum obtained in a state in which the concave portion is not formed with the infrared spectrum of the known plastic, surface treatment agent and impurity, thereby detecting the surface treatment agent and impurity attached to the test piece.

With this preferable example, not only the kind of plastic material but also the surface treatment agent and impurity attached to the surface can be detected.

In the above-mentioned first to third methods, it is preferable that at least a part of the surface of the crystal is spherical and that the spherical part is brought into contact with the test piece. With such a preferable example, the test piece can be brought into contact with the crystal in a minute point. Thus, it is possible to measure the portion of the test piece to be measured with high precision even if it has a relatively small area.

Furthermore, in the first to third methods, an example of the plastic material to be tested includes, for example, a waste plastic.

In order to achieve the above-mentioned object, a first plastic distinguishing apparatus of the present invention includes a measurement part (including a crystal for attenuated total reflection spectroscopy and an infrared spectrometer) for measuring an infrared spectrum of a test piece of a plastic material by attenuated total reflection spectroscopy, a holding part for holding the test piece in a state in which the test piece is brought into contact with the crystal, and a distinguishing part for comparing the infrared spectrum of the test piece with the infrared spectrum of the known plastic, wherein the holding part holds the test piece having a section in a state in which this section is brought into contact with the crystal.

By using such an apparatus, it is possible to carry out the first method of the present invention efficiently.

It is preferable that the first apparatus further includes a cutting part for preparing the test piece by cutting the plastic material. It is advantageous because a test piece can be prepared further speedily and simply. An example of the cutting part includes one provided with, for example, a punching machine, a shearing machine, or a band saw machine.

Furthermore, in the first apparatus, it is preferable that the holding part holds the test piece in a state in which a part of the section corresponding to the inside portion of the plastic material is brought into contact with the crystal and in a state in which a part of the section corresponding to the surface portion of the plastic material is brought into contact with the crystal; the measurement part measures an infrared spectrum of the test piece in the part corresponding to the inside portion of the plastic material and in the part corresponding to the surface portion of the plastic material; the distinguishing part compares the infrared spectrum obtained in the part corresponding to the inside portion of the plastic material with the infrared spectrum of the known plastic, thereby distinguishing the kind of plastic constituting the test piece, and compares the infrared spectrum obtained in the part corresponding to the surface portion of the plastic material with the infrared spectrum of the known plastic, surface treatment agent and impurity, thereby detecting the surface treatment agent and impurity attached to the test piece.

With such a preferable example, not only the kind of plastic material but also the surface treatment agent and impurity attached to the surface can be detected.

Furthermore, in the first apparatus, it is preferable that the holding part holds the test piece in a state in which the section of the test piece is brought into contact with the crystal and in a state in which a part of the test piece other than the section is brought into contact with the crystal; the measurement part measures the infrared spectrum of the test piece in the section and in the part other than the section; the distinguishing part compares the infrared spectrum obtained in the section with the infrared spectrum of the known plastic, thereby distinguishing the kind of plastic constituting the test piece, and compares the infrared spectrum obtained in the part other than the section with the infrared spectrum of the known plastic, surface treatment agent and impurity, thereby detecting the surface treatment agent and impurity attached to the test piece.

Also with this a preferable example, not only the kind of plastic material but also the surface treatment agent and impurity attached to the surface can be detected.

In order to achieve the above-mentioned object, a second plastic distinguishing apparatus of the present invention includes a processing part for forming a concave portion on a surface of a test piece of a plastic material by applying pressure to the surface of the test piece, a measurement part (including a crystal for attenuated total reflection spectroscopy and an infrared spectrometer) for measuring an infrared spectrum of the test piece by attenuated total reflection spectroscopy, a holding part for holding the test piece in a state in which the test piece is brought into contact with the crystal, and a distinguishing part for comparing the infrared spectrum of the test piece and an infrared spectrum of a known plastic, wherein the holding part holds the test piece in a state in which the crystal is brought into contact with the concave portion formed in the processing portion.

By using such an apparatus, it is possible to carry out the second method of the present invention efficiently.

Furthermore, in the second apparatus, it is preferable that the holding part holds the test piece in a state in which the crystal is brought into contact with the concave portion of the test piece and in a state in which the crystal is brought into contact with a part of the test piece in which the concave portion is not formed; the measurement part measures an infrared spectrum of the test piece in the concave portion and the part in which the concave portion is not formed; the distinguishing part compares the infrared spectrum measured in the concave portion with the infrared spectrum of the known plastic, thereby distinguishing the kind of plastic constituting the test piece, and compares the infrared spectrum measured in the part in which the concave portion is not formed with the infrared spectrum of the known plastic, surface treatment agent and impurity, thereby detecting the surface treatment agent and impurity attached to the test piece.

With such a preferable example, not only the kind of plastic material but also the surface treatment agent and impurity attached to the surface can be detected.

In order to achieve the above-mentioned object, a third plastic distinguishing apparatus of the present invention includes a measurement part (including a crystal for attenuated total reflection spectroscopy and an infrared spectrometer) for measuring an infrared spectrum of the test piece of the plastic material by attenuated total reflection spectroscopy, a holding part for holding the test piece in a state in which the test piece is brought into contact with the crystal, a contact pressure control part for controlling the contact pressure between the test piece and the crystal, and a distinguishing part for comparing the infrared spectrum of the test piece with the infrared spectrum of the known plastic, wherein the contact pressure control part controls the contact pressure between the test piece and the crystal to be such a pressure that a concave portion is formed in a part of the test piece being in contact with the crystal.

By using such an apparatus, it is possible to carry out the third method of the present invention efficiently.

Furthermore, in the third apparatus, it is preferable that the contact pressure control part controls the contact pressure to be such a pressure that the concave portion is formed in the part of the test piece being in contact with the crystal and to be such a pressure that the concave portion is not formed, the measurement part measures an infrared spectrum of the test piece in a state in which the concave portion is formed and in a state in which the concave portion is not formed, the distinguishing part compares the infrared spectrum measured in a state in which the concave portion is formed with the infrared spectrum of the known plastic, thereby distinguishing the kind of plastic constituting the test piece; and compares the infrared spectrum measured in a state in which the concave portion is not formed with the infrared spectrum of the known plastic, surface treatment agent and impurity, thereby detecting the surface treatment agent and impurity attached to the test piece.

With such a preferable example, not only the kind of plastic materials but also the surface treatment agent and impurity attached to the surface can be detected.

In the first to third apparatus, it is preferable that at least a part of the surface of the crystal is spherical and that the spherical part is brought into contact with the test piece. It is advantageous because high precise measurement can be carried out even if the test piece has a relatively small area.

BEST MODE OF CARRYING OUT THE INVENTION

First Embodiment

Figure 1:
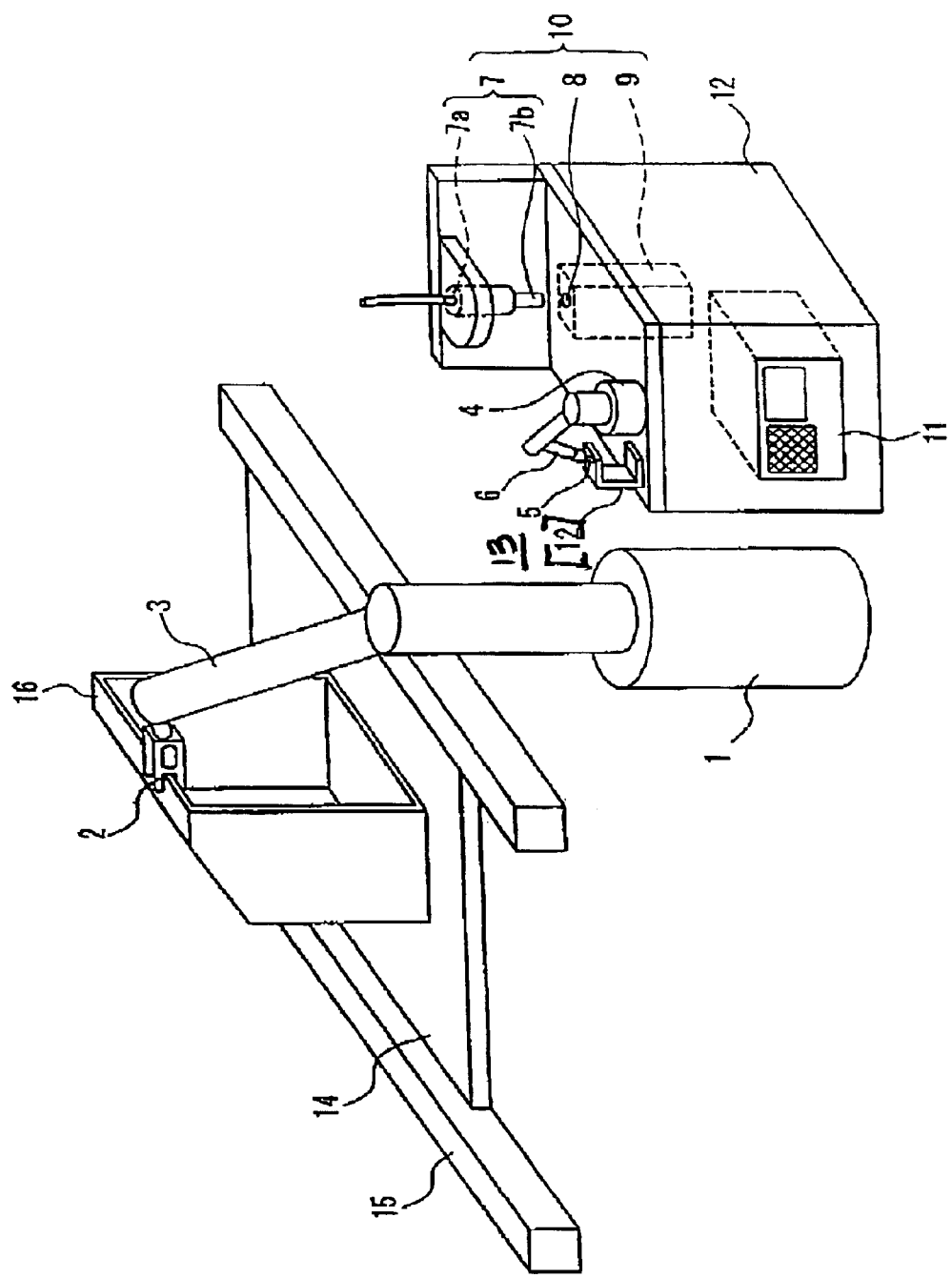
FIG. 1 is a perspective view showing a plastic distinguishing apparatus according to a first embodiment of the present invention.

The following is an example for a structure of a plastic distinguishing apparatus of the present invention. FIG. 1 is a perspective view showing one example of a configuration of the plastic distinguishing apparatus.

This plastic distinguishing apparatus includes a cutting part 1, a holding part 4, a measurement part 10 and a distinguishing part 11 as main component elements.

The cutting part 1 is a part for preparing a test piece by cutting a plastic material 16 to be tested. In the apparatus shown in FIG. 1, as a cutting part 1, a robot (first robot) provided with a cutting machine 2 at the tip of the arm 3 is used. This first robot has also a function of carrying the obtained test piece to a test piece stand 13.

It is preferable that the cutting machine 2 can realize cutting with a cutter. Furthermore, it is preferable that the cutting machine 2 cuts a subject (plastic material) by cutting not with a reciprocating shear but with one-way movement of the cutter. Examples of such a cutting machine 2 include, for example, a punching machine such as a punch press, a shearing machine such as a shear, a pincher, scissors, etc., a band saw machine, etc.

Figure 2:
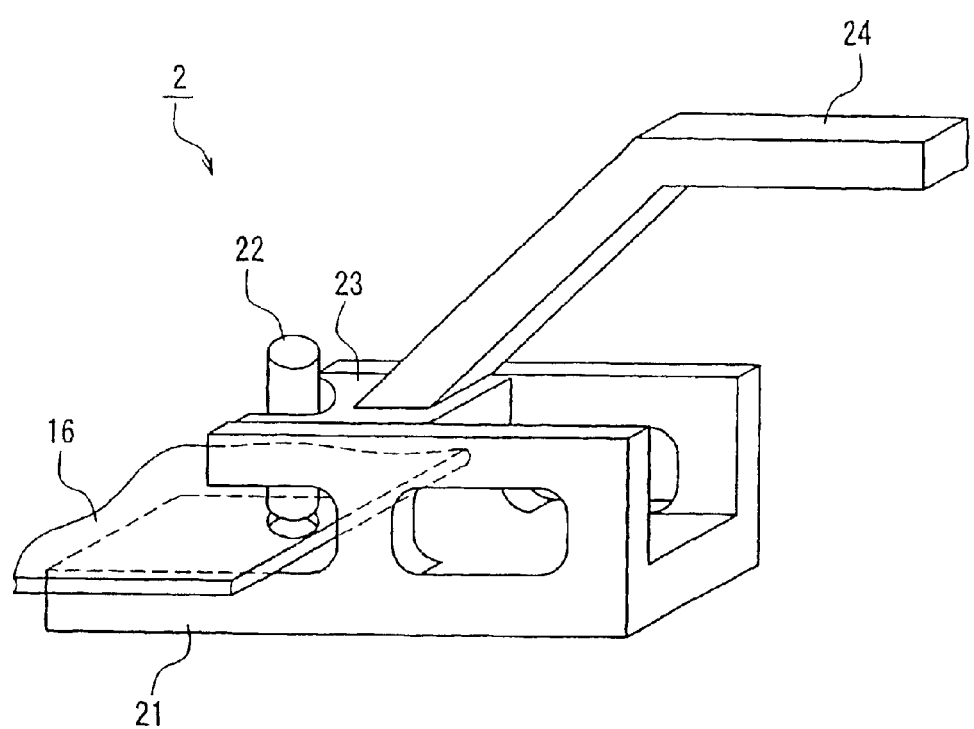
FIG. 2 is a perspective view showing an example of a cutting machine of a cutting portion.

FIG. 2 is a perspective view showing an example of a structure of a cutting machine 2. This cutting machine 2 is provided with a die 21, a punch 22 and a press mechanism (including a handle 24 and a toggle 23) for moving the punch 22. This cutting machine 2 can cut the plastic material 16 into a desired shape by disposing the plastic material 16 with the die 21, operating the toggle by pushing the handle 24 and punching the plastic material 16 with the punch 22.

The holding part 4 is a part for holding a test piece and disposes it on the measurement part in a predetermined state (a way of setting the test piece will be explained later). In the apparatus shown in FIG. 1, as the holder part 4, a robot (second robot) provided with a band 5 at the tip of the arm 6 is used. This band 5 is, for example, a gripper type hand, a multi-finger/multi-articulation hand.

The measurement part 10 is a part for measuring an infrared spectrum of a test piece. This measurement part 10 includes a crystal 8, a test piece pressing mechanism 7 and an infrared spectrum measurement device 9.

The crystal 8 is transparent and is not absorptive with respect to the infrared region, and has a refractive index that is higher than that of a plastic material to be tested. As materials for such a crystal, it is possible to use well-known material as a crystal that can be used for the ATR. An example of such a material includes, for example, Ge, Si, ZnSe, KRS-5 (a mixed crystal of thallium bromide and thallium iodide), etc.

Furthermore, this crystal 8 has a spherical surface in at least a part of the surface and is disposed so that the test piece is brought into contact with the spherical surface when measurement is carried out. The shape of the crystal 8 is designed so that light entering the crystal is converged into the spherical part of the crystal where the test piece is brought into contact, and further into a contact portion between the spherical part and the test piece.

The test piece pressing mechanism part 7 includes a pressing rod 7b for pressing the test piece onto the crystal 8 and a pressing mechanism part 7a for moving the pressing rod 7b. It is preferable that the pressing mechanism part 7a can control the pressure freely so as to change the contact pressure between the test piece and the crystal. For example, it may be a hydraulic cylinder, etc. Furthermore, it is preferable that the test piece pressing mechanism part 7 includes a pressure detection mechanism part for detecting the contact pressure between the test piece and the crystal and a pressure control mechanism for controlling the pressing mechanism based on the data detected by the pressure detection mechanism. With such an apparatus, the contact pressure between the test piece and the crystal can be set within the predetermined range by operating the pressing mechanism part so as to bring the test piece into close contact with the crystal by a pressing rod; detecting the contact pressure between the test piece and the crystal in the pressure detection mechanism part; and further operating the pressing mechanism part to move the pressing rod up and down appropriately by the pressure control portion when the detected contact pressure is out of the set range.

The infrared spectrum measurement device 9 includes an infrared light source, an optical system for leading light from the light source to the crystal (preferably, this system includes an incident angle control portion for controlling the incident angle of light with respect to the interface between the test piece and the crystal), an optical system for leading light reflected from the interface to a spectrometer, and a spectrometer for detecting the reflected light and measuring the spectrum thereof. Furthermore, the infrared spectrum measurement device may use a Fourier transform spectroscopy.

The distinguishing part 11 is a part for comparing the infrared spectrum of the test piece and the infrared spectrum of the known plastic. This distinguishing part 11 includes a first memory part in which the infrared spectrum of the test piece obtained in the measurement part 10 (hereinafter, also "spectrum of unknown sample" will be referred to) is recorded, and a second memory part in which infrared spectra of the various kinds of known plastics are recorded. In addition, it is preferable that the infrared spectrum of the known surface treatment agent and impurity is recorded in the second memory part (hereinafter, the infrared spectrum of the known plastic, known surface treatment agent and impurity also will be referred to as "spectrum of known sample").

As the spectrum of known sample, for example, prior to testing plastic material to be tested, the infrared spectra of the known plastic, surface treatment agent and impurity are measured by the plastic distinguishing apparatus, and this can be used by recording it in the second memory part.

Furthermore, the distinguishing part 11 includes a detection part for comparing the spectrum of unknown sample recorded in the first memory part and the spectrum of known sample recorded in the second memory part, thus detecting the spectrum of known sample corresponding to the spectrum of unknown sample.

Note here that in the apparatus shown in FIG. 1, the measurement part 10 and the distinguishing part 11 are incorporated in or attached to the apparatus main body 12.

Furthermore, it is preferable that the plastic distinguishing apparatus includes a pallet 14 and a conveyor 15 for carrying a subject to be tested to a place where the subject can be processed by the cutting portion.

Second Embodiment

Next, an example of the method for distinguishing the kind of plastic by the use of the above-mentioned plastic distinguishing apparatus will be explained.

Firstly, the plastic material 16 to be tested (for example, a waste plastic) is disposed on the pallet 14 and the conveyor 15 is operated, thus carrying the plastic material 16 to a place where it can be cut by the first robot 1 (that is, the cutting portion).

Subsequently, the first robot 1 is operated and a part of the plastic material 16 is cut by a cutting machine 2 attached to the tip thereof, thereby preparing a test piece. Note here that the shape and the size of the test piece is not particularly limited insofar as the test piece can be held by the second robot (that is, a holding part 4).

Figure 3:
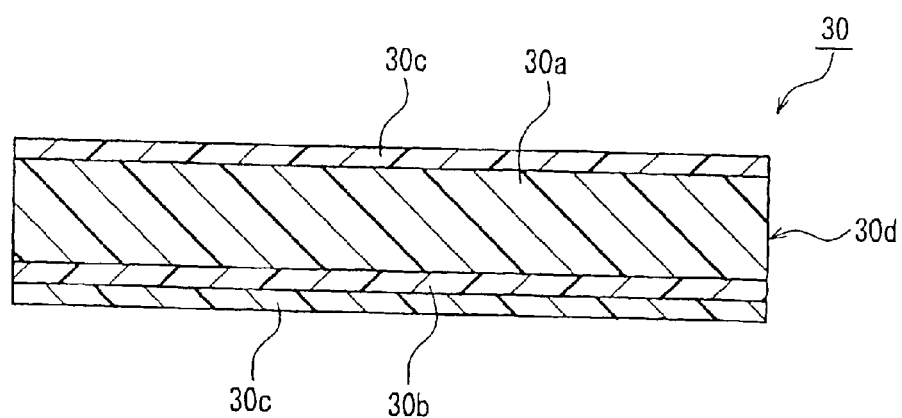
FIG. 3 is a cross-sectional view showing an example of a test piece.

FIG. 3 is a cross-sectional view showing an example of the test piece. In the test piece 30 shown in FIG. 3, on one surface of the plastic material 30a, a surface treatment agent 30b and impurity 30c are attached and on the other surface, impurity 30c is attached. Note here that in FIG. 3, reference numeral 30d denotes a section formed by cutting for preparing the test piece.

Next, the first robot 1 is operated and the prepared test piece is disposed on the test piece stand 13. Then, the second robot 4 is operated, grasping the test piece by a hand 5 attached to the tip thereof. Furthermore, the second robot 4 is operated and the test piece is disposed on the crystal 8 of the measurement part 10, followed by operating the test piece pressing mechanism 7 to press the test piece onto the crystal 8.

Figure 4:
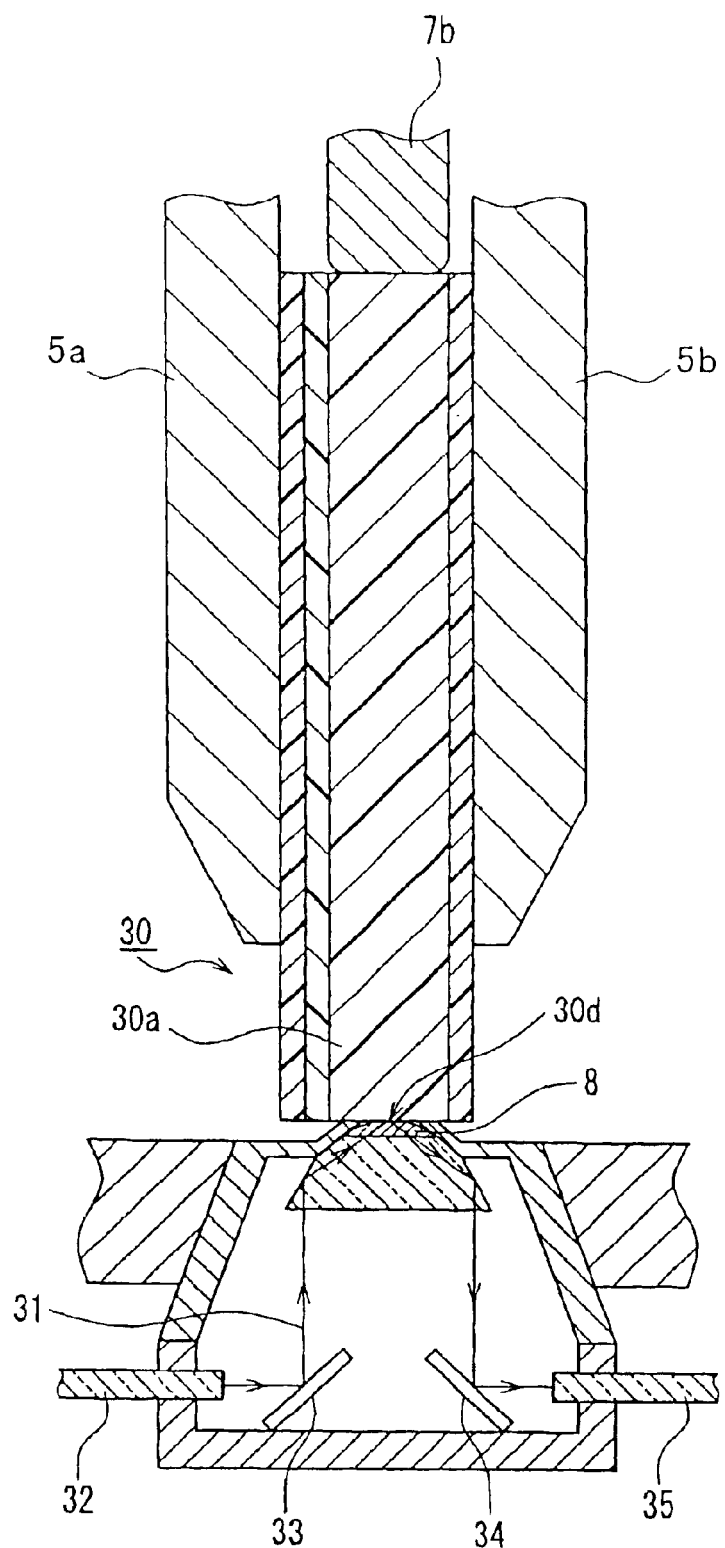
FIG. 4 is a cross-sectional view to explain a method for distinguishing plastics according to a second embodiment of the present invention, showing a state in which a test piece is brought into contact with a crystal for measuring an infrared spectrum.

At this time, as shown in FIG. 4, the test piece 30 is disposed on the crystal 8 so that the section 30d formed by cutting for preparing the test piece is brought into contact with the crystal 8. By operating the test piece pressing mechanism in this state, the test piece 30 can be pressed by the pressing rod 7b and the section 30d of the test piece 30 can be brought into close contact with the crystal 8. Note here that the contact pressure between the test piece 30 and the crystal 8 at this time is not particularly limited but it is, for example, 1 MPa to 100 MPa.

Subsequently, as shown in FIG. 4, an infrared light 31 (wave number: for example, 400 to 5000 $cm^{-1}$) is made incident in the interface between the test piece 30 and the crystal 8 and is reflected from the interface, followed by measuring the reflected spectrum. Thus, the infrared spectrum of the test piece is obtained. Note here that the incident angle of the infrared light 31 respect to the interface is set so that if the test piece is not absorptive, total reflection occurs.

Note here that in the example shown in FIG. 4, the infrared light is led to a reflective mirror 33 by an optical fiber 32, and reflected herein and enters the interface. Furthermore, the infrared light reflected at the interface is reflected by a reflection mirror 34 and enters an optical fiber 35, and is introduced into the spectroscope by this optical fiber 35.

Then, in the distinguishing portion 11, the obtained infrared spectrum of the test piece and the infrared spectrum of the known plastic are compared and the infrared spectrum corresponding to the infrared spectrum of the test piece is extracted from among the infrared spectra of the known plastics, thereby distinguishing the kind of plastic constituting the test piece.

As mentioned above, in the above-mentioned method, the infrared spectrum is measured by bringing the crystal into contact with the section of the test piece. Even if a surface treatment agent or impurity is attached to the surface of a subject to be tested, as shown in FIG. 3, a plastic material is exposed to the section of the test piece without fail. Therefore, by measuring the infrared spectrum in this section, the kind of the plastic material constituting the subject to be tested can be distinguished exactly without the influence of the surface treatment agent and impurity. Furthermore, since the measurement is carried out in a state in which the test piece is prepared by cutting and the crystal is brought into contact with the section, it is not necessary to preliminarily treat the test piece for removing a surface treatment agent and impurity. Therefore, it is possible to distinguish plastics speedily and simply.

Third Embodiment

Furthermore, in the distinguishing method according to the second embodiment, it is preferable that the infrared spectrum is measured in a plurality of places in the section of the test piece. In this case, an infrared spectrum is measured in the central part of the section (corresponding to the inside of the subject to be tested) and the end of the section (corresponding to a surface layer portion of the subject to be tested), respectively.

Figure 5:
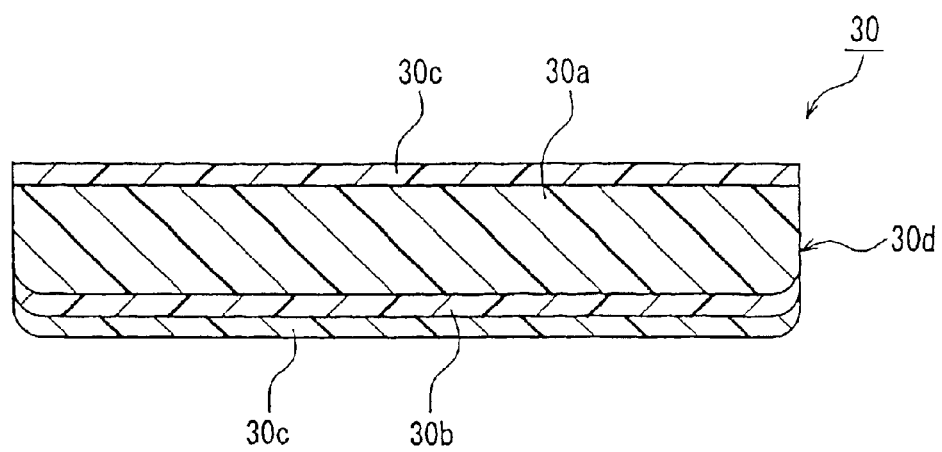
FIG. 5 is a cross-sectional view showing another example of a test piece.

In the end of the section, when the surface treatment agent or impurity is attached to the surface of the subject to be tested, the layers of these surface treatment agent and impurity are exposed. In particular, as the plastic material that is the subject to be tested is cut by a cutter in a cutting part and this cutting is carried out not with a reciprocating shear but by one-way movement of the cutter, as shown in FIG. 5, the layer of the surface treatment agent 30b and the impurity 30c are exposed to the end in a way in which they surrounds the section 30d.

Figure 6A:
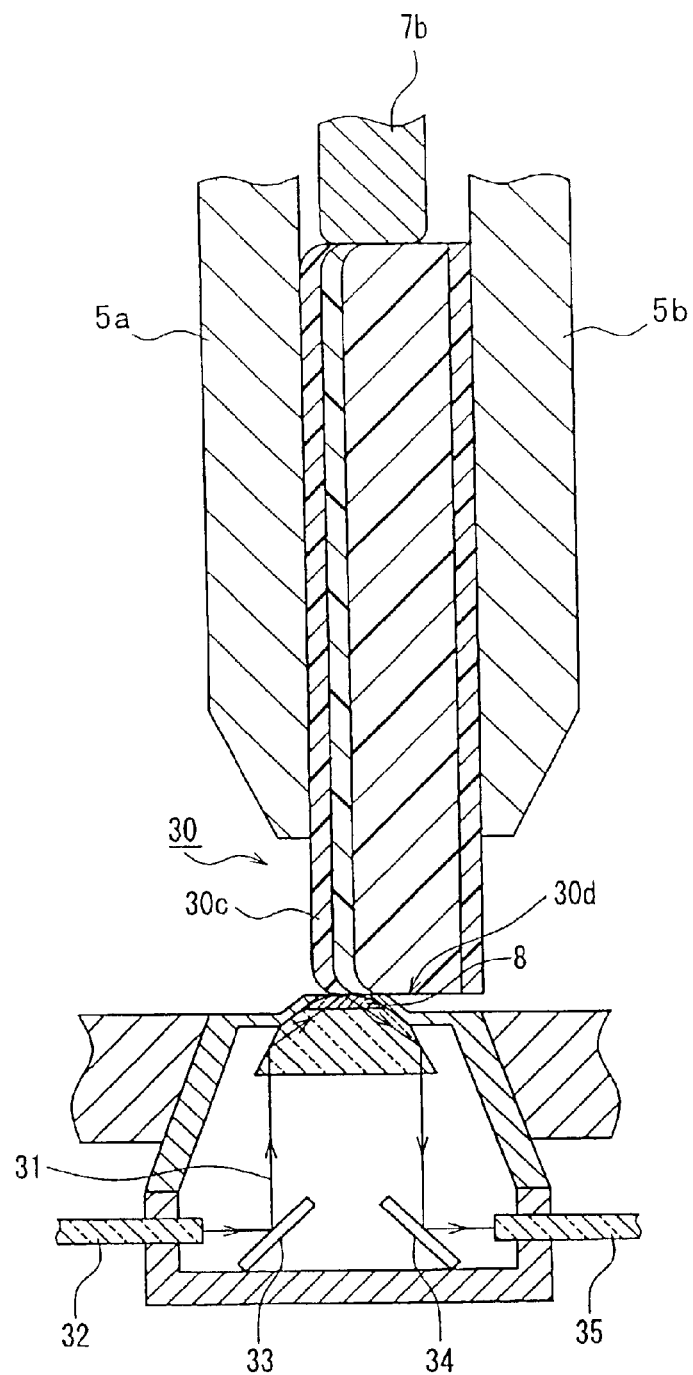
FIGS. 6A to 6C are cross-sectional views to explain a method for distinguishing plastics according to a third embodiment of the present invention, showing a state in which the end of a section of a test piece is brought into contact with a crystal (see FIGS. 6A and 6B) and a state in which the center of the section of a test piece is brought into contact with a crystal (see FIG. 6C) for measuring an infrared spectrum.
Figure 6B:
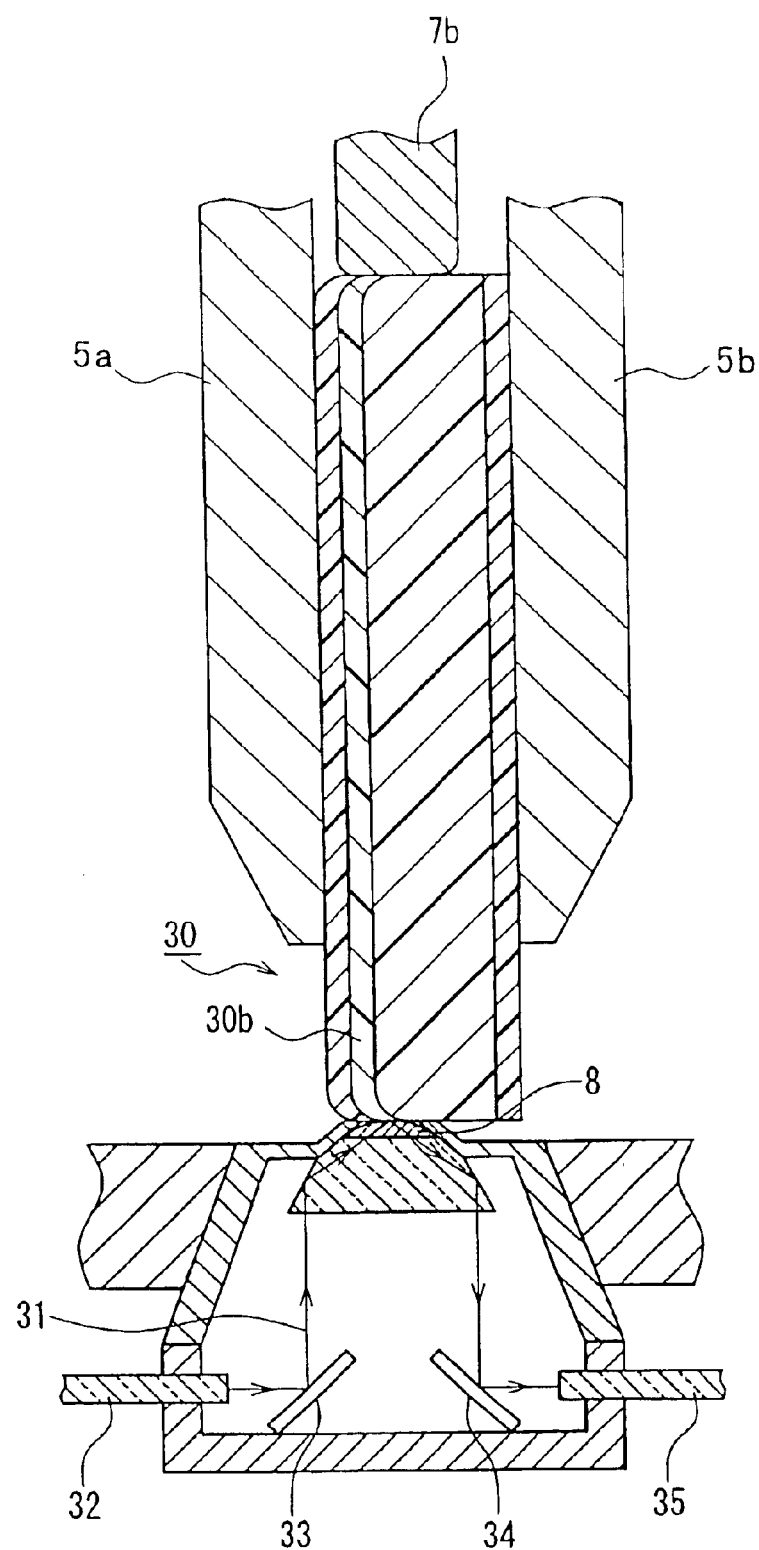

Therefore, when the infrared spectrum is measured by bringing the crystal into contact with the end of the section, if the surface treatment agent or impurity is attached to the surface of the subject to be tested, the infrared spectrum of the surface treatment agent or impurity is obtained. For example, as shown in FIG. 6A, when the crystal 8 is brought into contact with the portion of the end of the section 30d where the impurity 30c is exposed, the infrared spectrum of the impurity 30c can be obtained. Furthermore, as shown in FIG. 6B, by shifting the position of the test piece 30 and bringing the crystal 8 into contact with the portion where the surface treatment agent 30b is exposed, the infrared spectrum of the surface treatment agent 30b can be obtained. When the surface treatment agent or impurity is not attached to the surface of the subject to be tested, the infrared spectrum of the plastic material constituting the subject to be tested can be obtained.

In other words, the infrared spectrum measured in the end of the section will correspond to the infrared spectrum of the surface treatment agent and impurity when the surface treatment agent and impurity are attached, and the infrared spectrum measured in the end of the section will correspond to the infrared spectrum of the known plastic when a surface treatment agent and impurity are not attached.

Figure 6C:
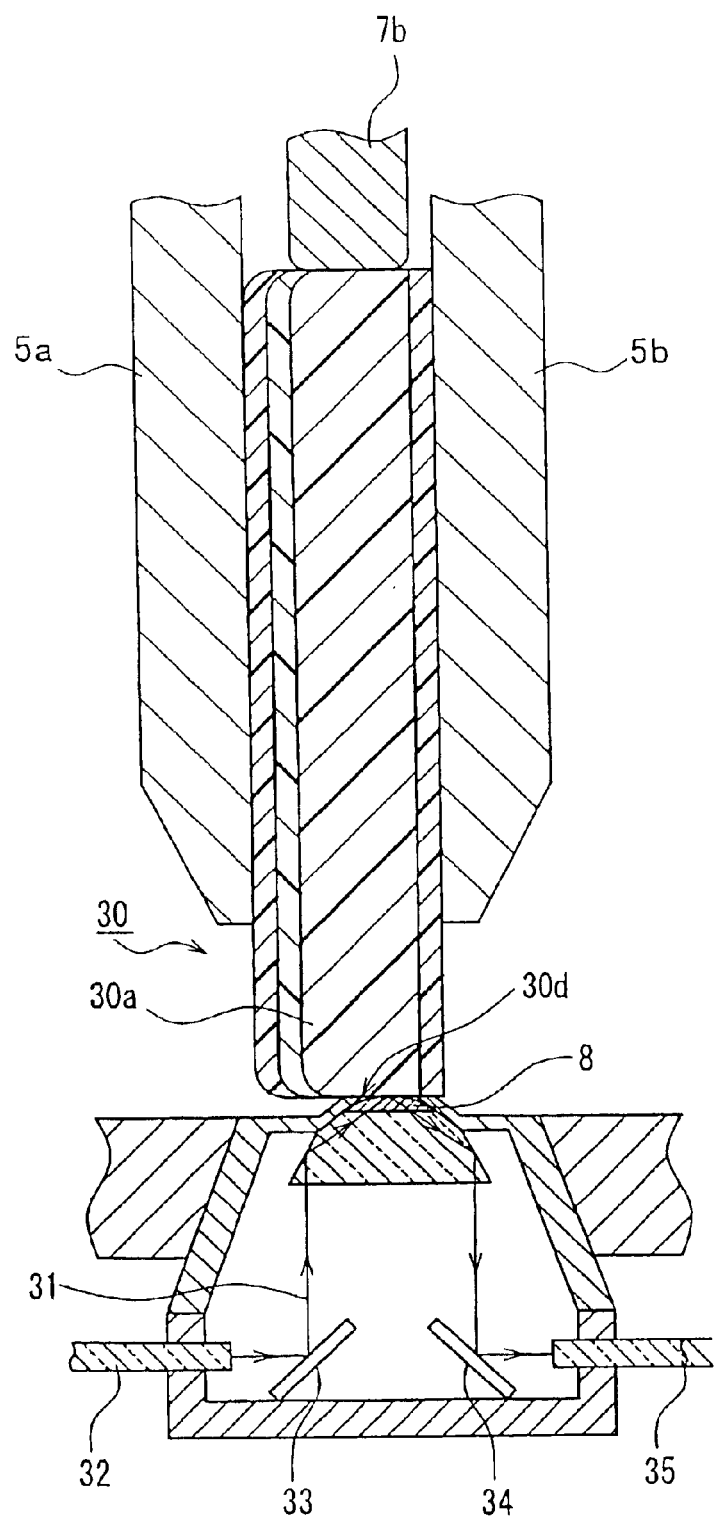

On the other hand, as mentioned above, regardless of the surface treatment agent and impurity on the surface of the subject to be tested, in the central portion of the section, the plastic material constituting the subject to be tested is exposed. Therefore, as shown in FIG. 6C, when the infrared spectrum is measured by bringing the crystal 8 into contact with the central portion of the section 30d, the infrared spectrum of the plastic material 30a constituting a subject to be tested can be obtained.

In this way, by measuring the infrared spectrum in a plurality of places in the section, the presence or absence of the surface treatment agent and impurity attached on the surface of the test piece can be detected. If the surface treatment agent and impurity are attached, the kind or attached amount thereof can be detected.

Furthermore, for example, if the measurement is carried out plural times while shifting the contact portion between the test piece and the crystal from the end portion to the central portion of the section, in the case where a plurality of layers of surface treatment agent and impurity are present, it is possible to detect the component and attached amount for every layer.

Fourth Embodiment

Furthermore, in the distinguishing method according to the second embodiment, it is preferable that, in addition to a step (hereinafter, "first measurement step" will be referred to) for measuring the infrared spectrum in the section of the test piece, a step (hereinafter, "second measurement step" will be referred to) for measuring the infrared spectrum in the surface other than the section of the test piece is carried out.

Figure 7:
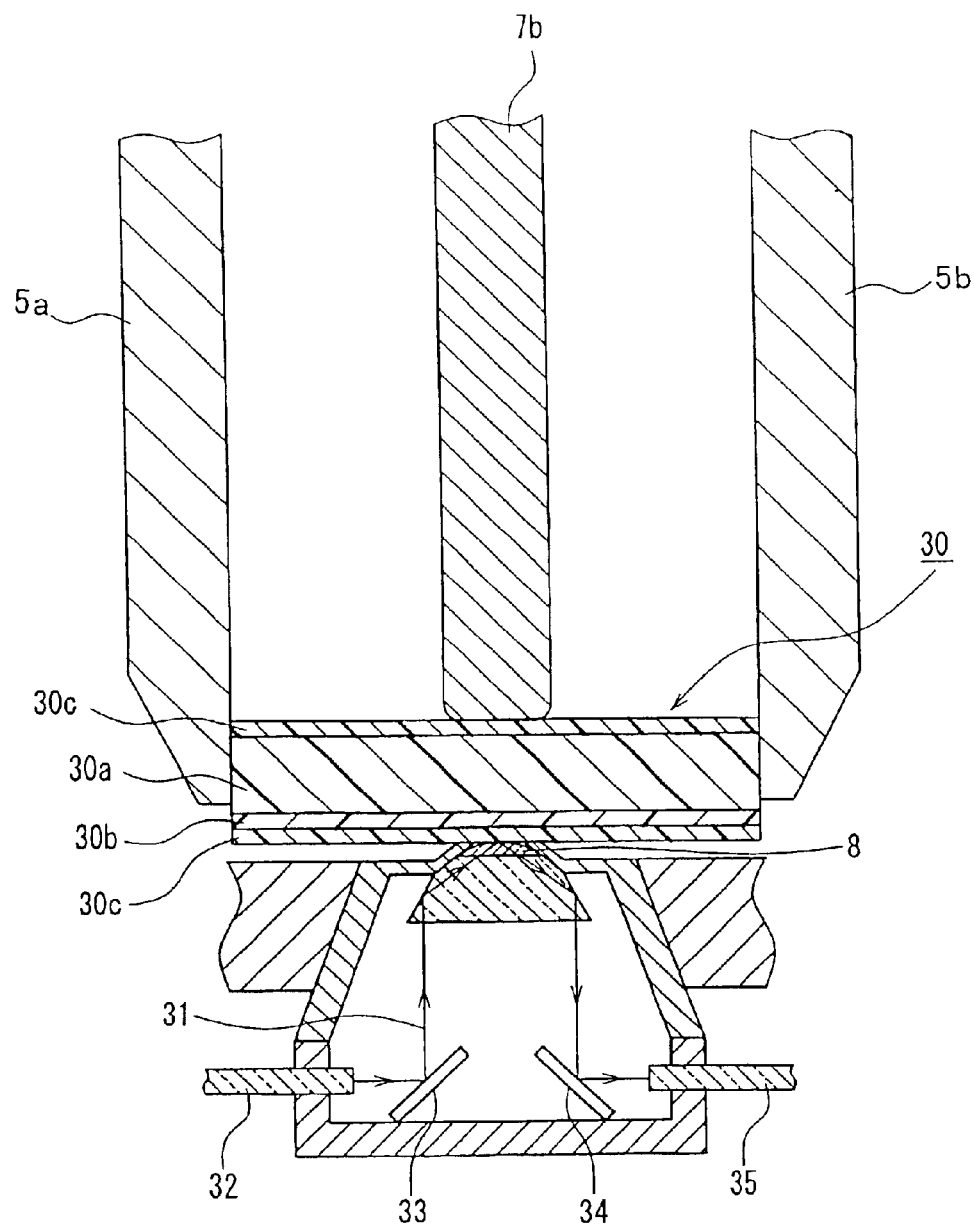
FIG. 7 is a cross-sectional view to explain one example of a method for distinguishing plastics according to a fourth embodiment of the present invention, showing a state in which a test piece is brought into contact with a crystal for measuring an infrared spectrum in the second measurement step.

The second measurement step, as shown in FIG. 7, can be carried out by the same operation as mentioned above except that the test piece 30 is disposed so that the surface other than the section is brought into contact with the crystal 8. At this time, the contact pressure between the test piece and the crystal is set to be, for example, 100 MPa or less, preferably 1 MPa to 50 MPa.

Then, the obtained infrared spectrum of the test piece is compared with the spectrum of known sample and the infrared spectrum corresponding to the infrared spectrum of the test piece is extracted from the spectra of known sample. At this time, the obtained infrared spectrum of the test piece will correspond to the infrared spectrum of the surface treatment agent and impurity when the surface treatment agent and impurity are attached, and the obtained infrared spectrum will correspond to the infrared spectrum of the known plastic when a surface treatment agent and impurity are not attached.

Therefore, by adding the second measurement step, the presence or absence of the surface treatment agent and impurity can be detected. If the surface treatment agent and impurity are attached, the kind and attached amount, etc. thereof can be detected.

Furthermore, in addition to the first and second measurement steps, the measurement step may be carried out in yet another surface other than the section. That is, with respect to one test piece, by changing the surface to be measured, measurement may be carried out three times or more in total.

Fifth Embodiment

Next, yet another example of a method for distinguishing plastics of the present invention will be explained. The method in this embodiment can be carried out by using a plastic distinguishing apparatus same as in FIG. 1.

Firstly, by operating the first robot 1, a part of the plastic material 16 that is the subject to be tested is cut so as to prepare the test piece, and the test piece is disposed on the test piece stand 13. Note here that the steps hereto can be carried out by the same method explained in the second embodiment.

Then, the second robot 4 is operated, grasping the test piece by hands 5a and 5b attached to the tip thereof. Furthermore, the second robot 4 is operated and the test piece is disposed on the crystal 8 of the measurement part 10, followed by operating the test piece pressing mechanism 7 so as to press the test piece onto the crystal 8.

Figure 8A:
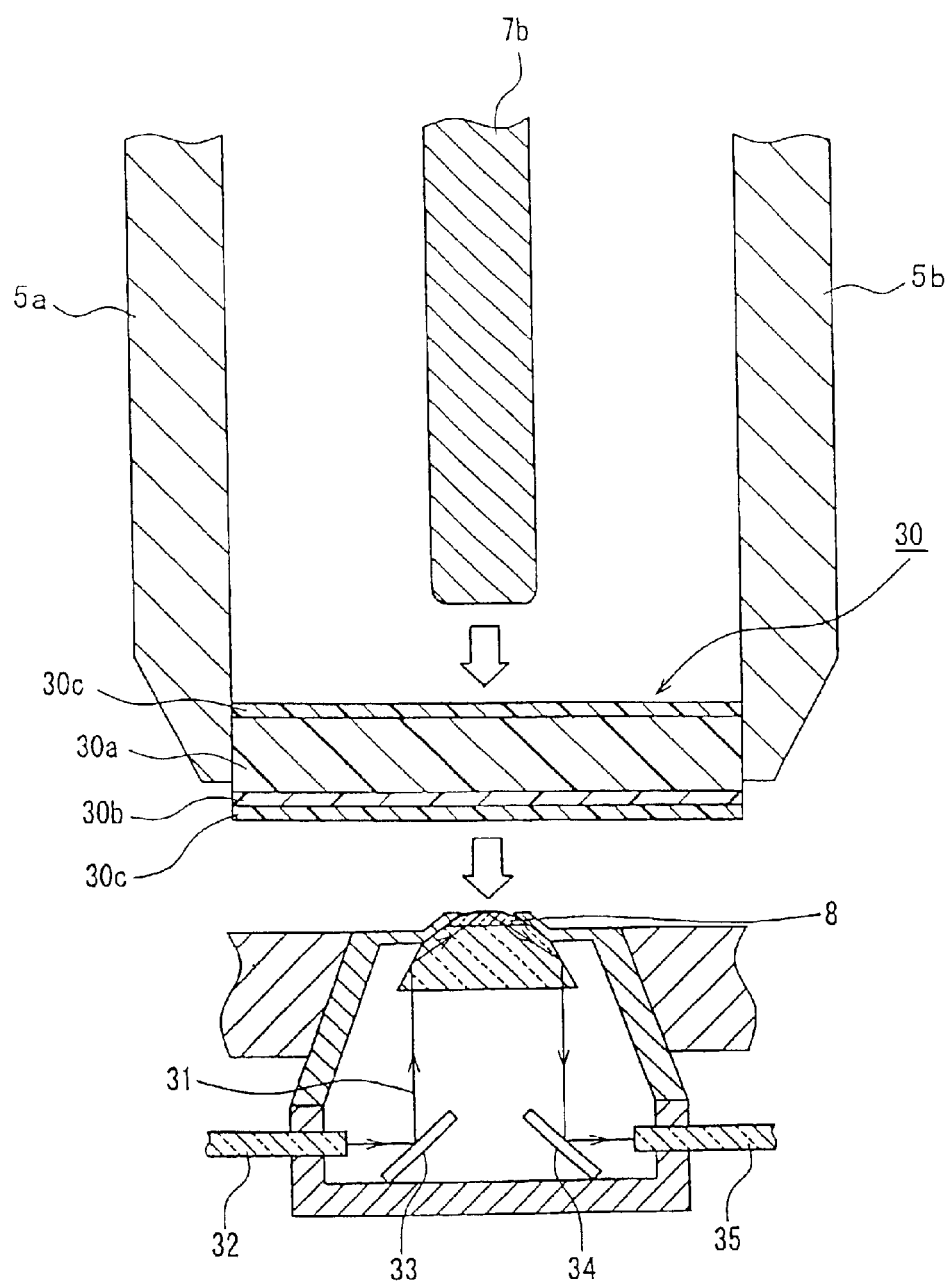
FIGS. 8A and 8B are cross-sectional views to explain a method for distinguishing plastics according to a fifth embodiment of the present invention, showing a state in which a test piece is brought into contact with a crystal (see FIG. 8A) and a state in which a concave portion is formed in the surface of the test piece (see FIG. 8B) for measuring an infrared spectrum.

At this time, as shown in FIG. 8A, the test piece is disposed on the crystal 8 so that the surface other than the section is brought into contact with the crystal 8. By operating the test piece pressing mechanism in this state, the test piece 30 can be pressed by the pressing rod 7b and the surface other than the section of the test piece 30 can be brought into contact with the crystal 8.

Figure 8B:
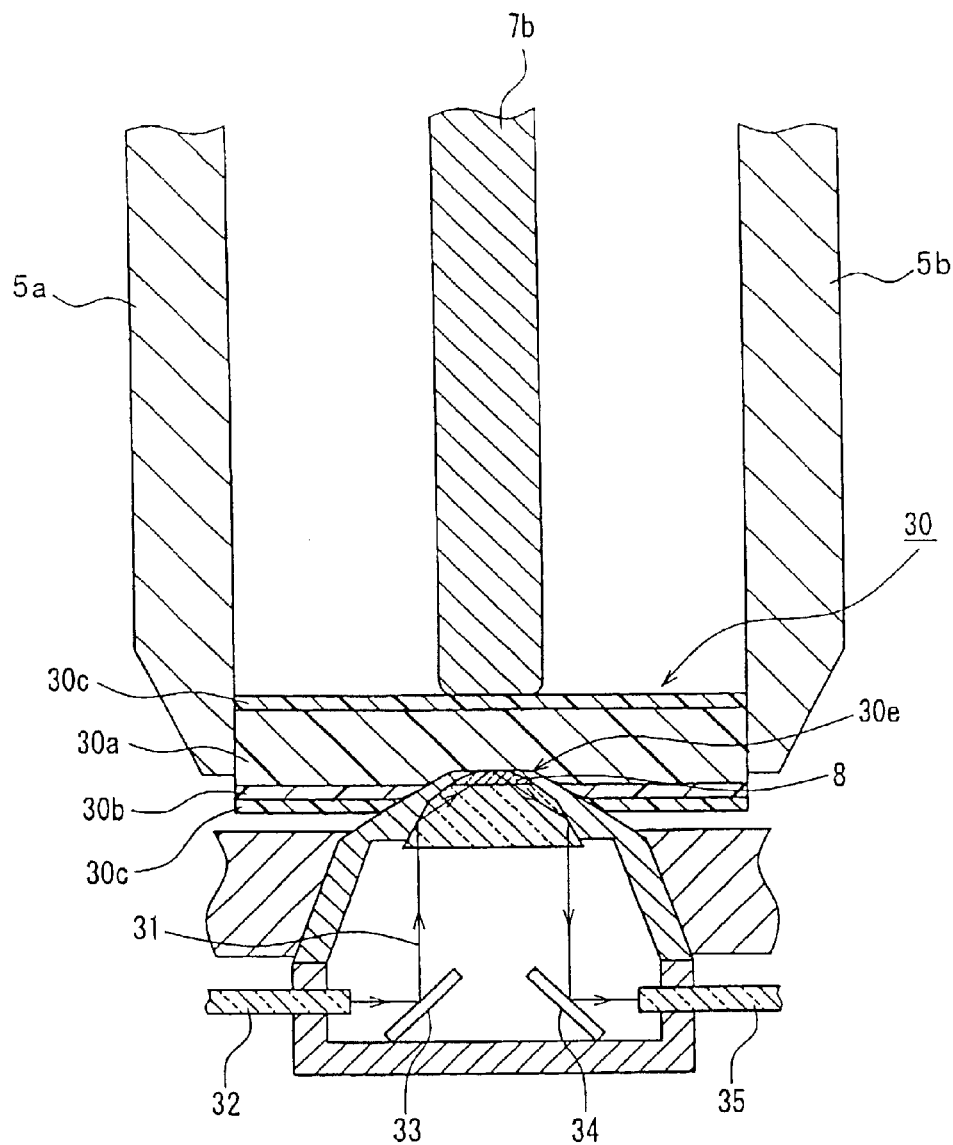

Subsequently, as shown in FIG. 8B, by operating the test piece pressing mechanism, pressure is applied to the test piece 30 by the pressing rod 7b, thus increasing the contact pressure between the test piece 30 and the crystal 8. Thus, in the portion of the test piece 30 where the crystal 8 is brought into contact, a concave portion 30e is formed. Note here that the contact pressure between the test piece 30 and the crystal 8 is not particularly limited but it is, for example, 50 MPa to 500 MPa, and preferably 100 MPa to 300 MPa.

Subsequently, in the measurement part 10, infrared spectrum of the test piece is obtained. At this time, since the concave potion 30e is formed in the portion of the test piece 30 where the crystal 8 is brought into contact, the measurement of the infrared spectrum is carried out with respect to the inside surface of the concave portion 30e. Next, in the distinguishing part 11, the obtained infrared spectrum of the test piece is compared with the infrared spectrum of the known plastic, thus distinguishing a kind of plastics constituting the test piece. Note here that this measurement step and the distinguishing step can be carried out similar to the method explained in the embodiment 2.

As mentioned above, in the above-mentioned method, by setting the contact pressure between the crystal and the test piece to relatively large, the concave portion is formed on the surface of the test piece. Then, in a state in which the crystal is brought into contact with the inside surface of the concave portion, the infrared spectrum is measured. In this way, by applying pressure to the surface of the test piece to form a concave portion, even if the surface treatment agent and impurity are attached to the surface of the subject to be tested, in the internal surface of the concave portion, the layer of the surface treatment agent and impurity is thinned or removed by being pushed away. Therefore, by measuring the infrared spectrum in the concave portion, it is possible to distinguish the kind of plastic constituting the subject to be tested exactly without much influence of the surface treatment agent and impurity. Furthermore, with respect to the test piece, particular pretreatment (shaving, etc.) for removing the surface treatment agent and impurity is not necessary.

Furthermore, in the distinguishing method according to this embodiment, as mentioned above, it is preferable that, in addition to the step (hereinafter, "first measurement step" will be referred to) for measuring an infrared spectrum in a state in which the contact pressure between the test piece and the crystal is set to be relatively large and a concave portion is formed on the surface of the test piece, a step (hereinafter "second measurement step" will be referred to) for measuring the infrared spectrum is measured in a state in which the contact pressure between the test piece and the crystal is made to be smaller than in the first measurement step.

This second measurement step can be carried out by the same operation as mentioned above except that the contact pressure between the test piece and the crystal is made to be small. At this time, the contact pressure between the test piece and the crystal is set to be smaller than that in the first measurement step. The contact pressure is set to the extent that the surface treatment agent and impurity are not completely removed by being pushed away when the surface treatment agent and the impurity are attached to the surface of the test piece, that is, to the extent that a concave portion is not formed on the surface of the test piece. An example of such a contact pressure is, for example 50 MPa or less, and preferably, 1 MPa to 30 MPa.

Then, the obtained infrared spectrum of the test piece is compared with the spectrum of known samples and the infrared spectrum corresponding to the infrared spectrum of the test piece is extracted from the spectra of known samples. At this time, the obtained infrared spectrum of the test piece will correspond to the infrared spectrum of the surface treatment agent and impurity when the surface treatment agent and impurity are attached, and the obtained infrared spectrum will correspond to the infrared spectrum of the known plastic when a surface treatment agent and impurity are not attached.

Therefore, by adding the second measurement step, the presence or absence of the surface treatment agent and impurity can be detected. If the surface treatment agent and impurity are attached, a kind or attached amount thereof can be detected.

Note here that the second measurement step is usually carried out prior to the first measurement step.

Furthermore, in addition to the first and second measurement steps, the measurement step may be carried out in which the contact pressure between the test piece and the crystal is varied may be added. That is, the measurement may be carried out three times or more in total while varying the contact pressure between the test piece and the crystal with respect to one test piece.

Sixth Embodiment

Next, another example of the plastic distinguishing apparatus of the present invention will be explained.

Similar to the first embodiment, this apparatus includes a cutting part 1, a holding part 4, a measurement part 10 and a distinguishing part 11. This apparatus further includes a processing part for forming a concave portion by applying pressure to the surface of the test piece. The structure of the processing part is not particularly limited, for example, a structure including a press stand on which a test piece is disposed, a pad for applying pressure to the test piece, and a press mechanism for moving the pad can be employed. Furthermore, it is preferable that the processing part can control the pressure applied to the test piece freely.

The apparatus according to this embodiment can have substantially the same structure as explained in the first embodiment except that the processing part is provided.

Next, an example of a plastic distinguishing method according to this embodiment will be explained.

Note here that the explanation below is the same as in the case where the method of this embodiment carried out by using the apparatus having the same configuration shown in FIG. 1 except that a processing part as mentioned above is provided and that the second robot carries the test piece on the test piece stand to the processing part and further carries the processed test piece to the measurement part.

Firstly, by operating the first robot, a part of the plastic material that is the subject to be tested is cut and the test piece is prepared, and this test piece is disposed on the test piece stand. Note here that the steps hereto can be carried out by the same method as explained in the second embodiment.

Figure 9A:
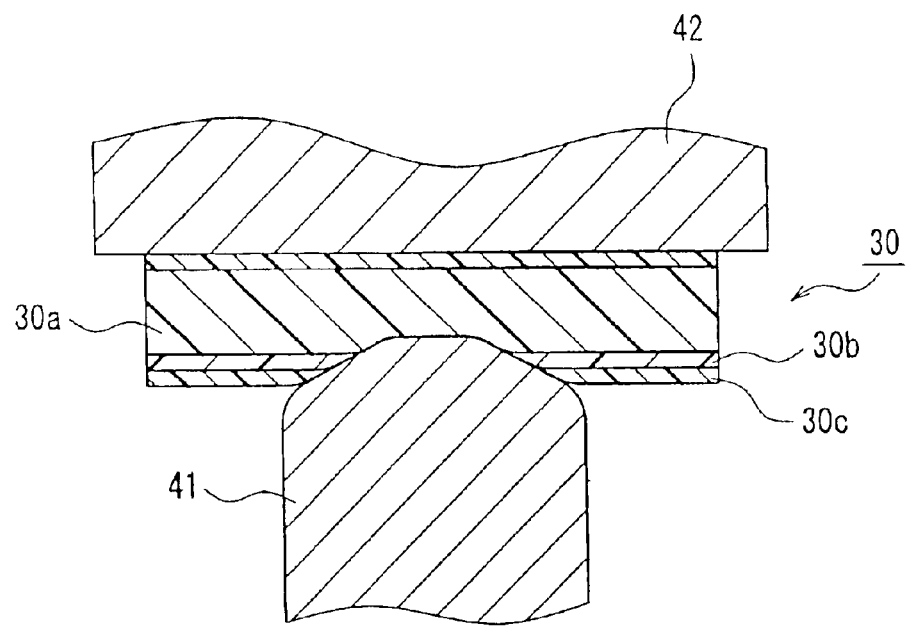
FIGS. 9A to 9C are cross-sectional views to explain a method for distinguishing plastics according to a sixth embodiment of the present invention, showing a state in which a concave portion is formed in the surface of the test piece (see FIGS. 9A and 9B) and a state in which the surface of the test piece is brought into contact with the crystal (see FIG. 9C).
Figure 9B:
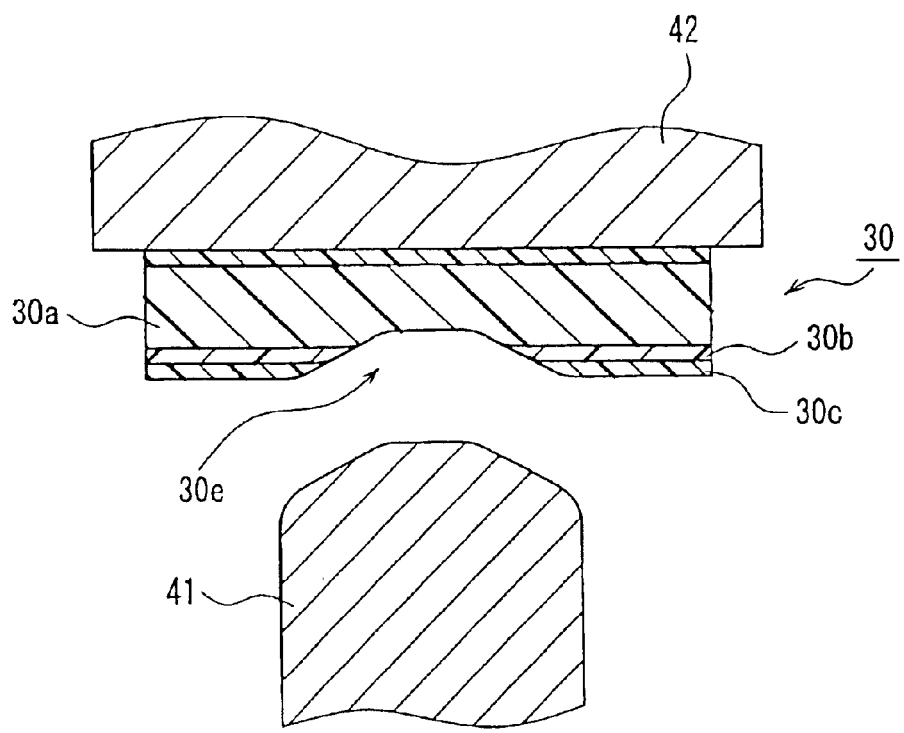

Then, the second robot is operated, grasping the test piece by the hand attached to the tip thereof and carrying it to the processing part. Next, as shown in FIG. 9A, the press mechanism of the processing part is operated and the pad 41 is pressed onto the surface of the test piece 30. Thereby, as shown in FIG. 9B, the concave portion 30e is formed on the surface of the test piece 30. Herein, the surface of the test piece is a surface other than the section formed for preparing the test piece. At this time, the pressure applied to the test piece is, for example, 100 MPa to 1000 MPa, and preferably 200 MPa to 500 MPa. The shape and the size of the concave portion is not particularly limited insofar as the crystal of the measurement part can be brought into contact with the inside surface of the concave portion. Note here that in FIGS. 9A and 9B, reference numeral 42 denotes a press stand.

Subsequently, the second robot is operated and the test piece is disposed on the crystal of the measurement part and then the test piece pressing mechanism is operated, pressing the test piece to the crystal.

Figure 9C:
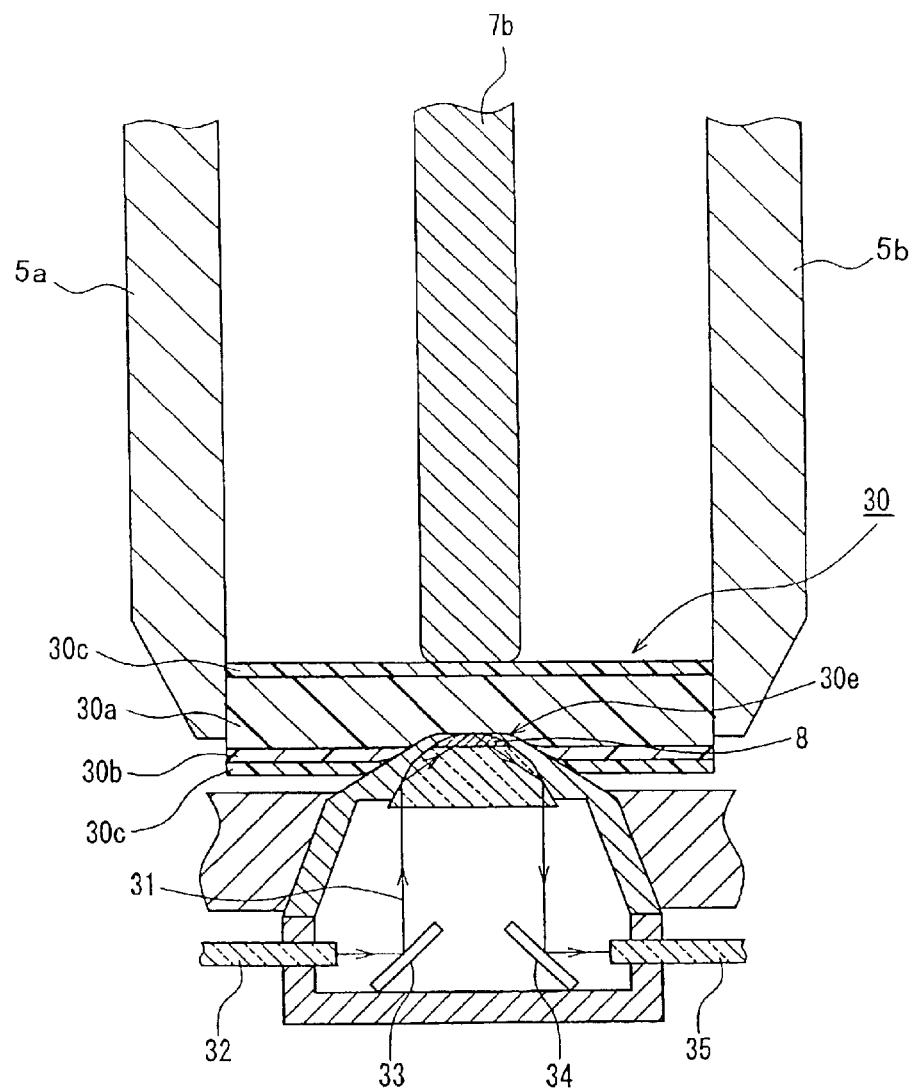

At this time, as shown in FIG. 9C, the test piece 30 is disposed on the crystal 8 so that the inside surface of the concave portion 30e formed in the processing part is brought into contact with the crystal 8. By operating the test piece pressing mechanism in this state, the test piece 30 is pressed with the pressing rod 7b and the inside surface of the concave portion 30e of the test piece 30 can be brought into close contact with the crystal 8.

Subsequently, in the measurement part, the infrared spectrum of the test piece is obtained; and the obtained infrared spectrum of the test piece is compared with the infrared spectrum of the known plastic, thereby distinguishing the kind of plastic constituting the test piece. Note here that this measurement step and the distinguishing step can be carried out by the same method as explained in the embodiment 2.

As mentioned above, in the above-mentioned method, by forming a concave portion by the press process on the surface of the test piece and bringing the crystal into contact with the inside surface of the concave portion, the infrared spectrum is measured. As in the method of the fourth embodiment, even if the surface treatment agent and impurity are attached to the surface of the subject to be tested, in the internal surface of the concave portion, the layer of the surface treatment agent and impurity is thinned or removed by being pushed away. Therefore, by measuring the infrared spectrum inside the surface of the concave portion, it is possible to distinguish the kind of plastic constituting the subject to be tested exactly. Furthermore, particular pretreatment (shaving, etc.) for removing the surface treatment agent and impurity is not necessary.

Furthermore, in the distinguishing method according to this embodiment, it is preferable that, in addition to the step (hereinafter, "first measurement step" will be referred to) in which a concave portion is formed on the test piece in the processing part and the infrared spectrum of the inside surface of the concave portion is measured, a step (herein after "second measurement step" will be referred to) for measuring the infrared spectrum in the portion of the test piece where the concave portion is not formed is carried out.

This second measurement step can be carried out by the same operation as mentioned above except that the contact portion between the test piece and the crystal is a portion other than the concave portion. Then, the obtained infrared spectrum of the test piece is compared with the spectrum of known sample. At this time, the obtained infrared spectrum of the test piece will correspond to the infrared spectrum of the surface treatment agent and impurity when the surface treatment agent and impurity are attached, and the obtained infrared spectrum will correspond to the infrared spectrum of the known plastic when a surface treatment agent and impurity are not attached.

Therefore, by adding the second measurement step, the presence or absence of the surface treatment agent and impurity can be detected. If the surface treatment agent and impurity are attached, the kind or attached amount thereof can be detected.

Furthermore, as another embodiment of the second measurement step of this embodiment, prior to forming the concave portion in the processing part, a step for measuring the infrared spectrum of the surface of the test piece may be carried out.

Furthermore, as another embodiment of the second measurement step of this embodiment, a step of applying pressure smaller than that of the first measurement step in the processing part and measuring the infrared spectrum in the portion where this pressure is applied may be carried out. In this case, in the second measurement step, the pressure applied to the test piece is set to the extent that the surface treatment agent and impurity are not completely removed by being pushed away when the surface treatment agent and the impurity are attached to the surface of the test piece, further to the extent that a concave portion is not formed on the surface of the test piece. An example of the pressure is, for example 50 MPa or less, and preferably, 1 MPa to 30 MPa. Furthermore, this second measurement step usually is carried out prior to the first measurement step.

Furthermore, by combining a plurality of embodiments as mentioned above in the second measurement step, the measurement is carried out three times or more in total with respect to one test piece.

INDUSTRIAL APPLICABILITY

As mentioned above, according to the present invention, it is possible to distinguish plastic materials speedily and simply with high precision. Furthermore, according to the preferable embodiment of the present invention, it is possible to detect not only the kind of plastic material but also the presence or absence of the surface treatment agent attached to the surface of the plastic and the kind and attachment amount thereof Thus, since it is possible to distinguish plastics speedily and simply with high precision, for example, by incorporating the method of the present invention into the processing step of recycling waste plastics contained in used household electrical appliances or automobiles, it is possible to promote recycling of plastic materials efficiently. Furthermore, when plastic materials are recycled, if surface treatment agent and impurity attached to the plastic materials can be detected, it is possible to select the suitable method for removing surface treatment agents and impurity based on the detection results, thus promoting the recycling more efficiently.

What is claimed is:

1. A method for distinguishing plastics, comprising:
preparing a test piece of a plastic material;
measuring an infrared spectrum of the test piece by attenuated total reflection spectroscopy; and
comparing the obtained infrared spectrum with an infrared spectrum of a known plastic, thereby distinguishing a kind of plastic materials,
wherein the test piece has a section and the infrared spectrum of the test piece is measured by bringing a crystal for attenuated total reflection spectroscopy into contact with the section of the test piece.

2. The method for distinguishing plastics according to claim 1, wherein at least a part of the surface of the crystal is spherical and this spherical part is brought into contact with the test piece.

3. The method for distinguishing plastics according to claim 1, wherein the test piece is prepared by cutting the plastic material by one selected from the group consisting of a punching machine, a shearing machine and a band saw machine.

4. The method for distinguishing plastics according to claim 1, wherein the infrared spectrum of the test piece is measured by bringing the crystal into contact with a part of the section corresponding to the inside portion of the plastic material and with a part of the section corresponding to the surface portion of the plastic material,
the infrared spectrum obtained in the part corresponding to the inside portion of the plastic material is compared with the infrared spectrum of the known plastic, thereby distinguishing a kind of plastic constituting the test piece, and
the infrared spectrum obtained in the part corresponding to the surface portion of the plastic material is compared with the infrared spectrum of the known plastic, surface treatment agent and impurity, thereby detecting the surface treatment agent and impurity attached to the test piece.

5. The method for distinguishing plastics according to claim 1, wherein the infrared spectrum of the test piece is measured by bringing the crystal into contact with the section of the test piece and with a part of the test piece other than the section,
the infrared spectrum obtained in the section is compared with the infrared spectrum of the known plastic, thereby distinguishing a kind of plastic constituting the test piece, and
the infrared spectrum obtained in the part other than the section is compared with the infrared spectrum of the known plastic, surface treatment agent and impurity, thereby detecting the surface treatment agent and impurity attached to the test piece.

6. The method for distinguishing plastics according to claim 1, wherein the plastic material is a waste plastic.

7. An apparatus for distinguishing plastics, comprising:
a measurement part for measuring an infrared spectrum of a test piece of a plastic material by attenuated total reflection spectroscopy, the measurement part comprising a crystal for attenuated total reflection spectroscopy and an infrared spectrometer,
a holding part for holding the test piece in a state in which the test piece is brought into contact with the crystal, and
a distinguishing part for comparing the infrared spectrum of the test piece with an infrared spectrum of a known plastic,
wherein the holding part holds the test piece having a section in a state in which this section is brought into contact with the crystal.

8. The plastic distinguishing apparatus according to claim 7, wherein at least a part of the surface of the crystal is spherical and this spherical part is brought into contact with the test piece.

9. The plastic distinguishing apparatus according to claim 7, further comprising a cutting part for preparing the test piece by cutting the plastic material.

10. The plastic distinguishing apparatus according to claim 9, wherein the cutting part comprises one selected from the group consisting of a punching machine, a shearing machine and a band saw machine.

11. The plastic distinguishing apparatus according to claim 7, wherein the holding part holds the test piece in a state in which a part of the section corresponding to the inside portion of the plastic material is brought into contact with the crystal and in a state in which a part of the section corresponding to the surface portion of the plastic material is brought into contact with the crystal;
the measurement part measures an infrared spectrum of the test piece in the part corresponding to the inside portion of the plastic material and in the part corresponding to the surface portion of the plastic material;
the distinguishing part compares the infrared spectrum obtained in the part corresponding to the inside portion of the plastic material with the infrared spectrum of the known plastic, thereby distinguishing a kind of plastic constituting the test piece, and compares the infrared spectrum obtained in the part corresponding to the surface portion of the plastic material with the infrared spectrum of the known plastic, surface treatment agent and impurity, thereby detecting the surface treatment agent and impurity attached to the test piece.

12. The plastic distinguishing apparatus according to claim 7, wherein the holding part holds the test piece in a state in which the section of the test piece is brought into contact with the crystal and in a state in which a part of the test piece other than the section is brought into contact with the crystal;
the measurement part measures the infrared spectrum of the test piece in the section and in the part other than the section;
the distinguishing part compares the infrared spectrum obtained in the section with the infrared spectrum of the known plastic, thereby distinguishing a kind of plastic constituting the test piece, and compares the infrared spectrum obtained in the part other than the section with the infrared spectrum of the known plastic, surface treatment agent and impurity, thereby detecting the surface treatment agent and impurity attached to the test piece.

13. A method for distinguishing plastics, comprising: preparing a test piece of a plastic material, measuring an infrared spectrum of the test piece by attenuated total reflection spectroscopy, and comparing the obtained infrared spectrum with an infrared spectrum of a known plastic, thereby distinguishing a kind of plastic material,
wherein the infrared spectrum of the test piece is measured by applying pressure to the surface of the test piece, forming a concave portion on the surface of the test piece applied pressure and bringing the concave portion into contact with the crystal for attenuated total reflection spectroscopy.

14. The method for distinguishing plastics according to claim 13, wherein at least a part of the surface of the crystal is spherical and this spherical part is brought into contact with the test piece.

15. The method for distinguishing plastics according to claim 13, wherein the infrared spectrum of the test piece is measured by bringing the crystal into contact with the concave portion of the test piece and with a part of the test piece in which the concave portion is not formed,
the infrared spectrum obtained in the concave portion is compared with the infrared spectrum of the known plastic, thereby distinguishing a kind of plastic constituting the test piece; and
the infrared spectrum obtained in the part in which the concave portion is not formed is compared with the infrared spectrum of the known plastic, surface treatment agent and impurity, thereby detecting the surface treatment agent and impurity attached to the test piece.

16. The method for distinguishing plastics according to claim 13, wherein the plastic material is a waste plastic.

17. An apparatus for distinguishing plastics, comprising:
a processing part for forming a concave portion on a surface of a test piece of a plastic material by applying pressure to the surface of the test piece;
a measurement part for measuring an infrared spectrum of the test piece by attenuated total reflection spectroscopy, the measurement part comprising a crystal for attenuated total reflection spectroscopy and an infrared spectrometer,
a holding part for holding the test piece in a state in which the test piece is brought into contact with the crystal, and
a distinguishing part for comparing the infrared spectrum of the test piece and an infrared spectrum of a known plastic,
wherein the holding part holds the test piece in a state in which the crystal is brought into contact with the concave portion formed in the processing portion.

18. The plastic distinguishing apparatus according to claim 17, wherein at least a part of the surface of the crystal is spherical and this spherical part is brought into contact with the test piece.

19. The plastic distinguishing apparatus according to claim 17, wherein the holding part holds the test piece in a state in which the crystal is brought into contact with the concave portion of the test piece and in a state in which the crystal is brought into contact with a part of the test piece in which the concave portion is not formed;
the measurement part measures an infrared spectrum of the test piece in the concave portion and the part in which the concave portion is not formed;

the distinguishing part compares the infrared spectrum measured in the concave portion with the infrared spectrum of the known plastic, thereby distinguishing a kind of plastic constituting the test piece, and compares the infrared spectrum measured in the part in which the concave portion is not formed with the infrared spectrum of the known plastic, surface treatment agent and impurity, thereby detecting the surface treatment agent and impurity attached to the test piece.

20. A method for distinguishing plastics, comprising:

preparing a test piece of a plastic material, measuring an infrared spectrum of the test piece by attenuated total reflection spectroscopy, and comparing the obtained infrared spectrum with an infrared spectrum of a known plastic, thereby distinguishing a kind of plastic material, wherein the infrared spectrum of the test piece is measured in a state in which a crystal for attenuated total reflection spectroscopy is brought into contact with the test piece, and a concave portion is formed in a part of the test piece in contact with the crystal by the contact pressure between the test piece and the crystal.

21. The method for distinguishing plastics according to claim 20, wherein at least a part of the surface of the crystal is spherical and the spherical part is brought into contact with the test piece.

22. The method for distinguishing plastics according to claim 20, wherein the infrared spectrum of the test piece is measured in a state in which the concave portion is formed in the part of the test piece being in contact with the crystal and in a state in which the concave portion is not formed in the part of the test piece being in contact with the crystal, the infrared spectrum obtained in a state in which the concave portion is formed is compared with the infrared spectrum of the known plastic, thereby distinguishing a kind of plastic constituting the test piece, and the infrared spectrum obtained in a state in which the concave portion is not formed with the infrared spectrum of the known plastic, surface treatment agent and impurity, thereby detecting the surface treatment agent and impurity attached to the test piece.

23. The method for distinguishing plastics according to claim 20, wherein the plastic material is a waste plastic.

24. An apparatus for distinguishing plastics, comprising:

a measurement part for measuring an infrared spectrum of a test piece of a plastic material by attenuated total reflection spectroscopy, the measurement part comprising a crystal for attenuated total reflection spectroscopy and an infrared spectrometer, a holding part for holding the test piece in a state in which the test piece is brought into contact with the crystal, a contact pressure control part for controlling the contact pressure between the test piece and the crystal, and a distinguishing part for comparing the infrared spectrum of the test piece with an infrared spectrum of a known plastic, wherein the contact pressure control part controls the contact pressure between the test piece and the crystal to be such a pressure that a concave portion is formed in a part of the test piece being in contact with the crystal.

25. The plastic distinguishing apparatus according to claim 24, wherein at least a part of the surface of the crystal is spherical and this spherical part is brought into contact with the test piece.

26. The plastic distinguishing apparatus according to claim 24, wherein the contact pressure control part controls the contact pressure to be such a pressure that the concave portion is formed in the part of the test piece being in contact with the crystal and to be such a pressure that the concave portion is not formed, the measurement part measures an infrared spectrum of the test piece in a state in which the concave portion is formed and in a state in which the concave portion is not formed, the distinguishing part compares the infrared spectrum measured in a state in which the concave portion is formed with the infrared spectrum of the known plastic, thereby distinguishing a kind of plastic constituting the test piece; and compares the infrared spectrum measured in a state in which the concave portion is not formed with the infrared spectrum of the known plastic, surface treatment agent and impurity, thereby detecting the surface treatment agent and impurity attached to the test piece.

* * * * *